(12) United States Patent
Furuichi et al.

(10) Patent No.: US 7,467,538 B2
(45) Date of Patent: Dec. 23, 2008

(54) GAS SENSOR AND METHOD FOR MANUFACTURING THE SAME

(75) Inventors: Toru Furuichi, Aichi (JP); Makoto Fukagai, Gifu (JP); Akio Mizutani, Aichi (JP)

(73) Assignee: NGK Spark Plug Co., Ltd., Aichi (JP)

( * ) Notice: Subject to any disclaimer, the term of this patent is extended or adjusted under 35 U.S.C. 154(b) by 102 days.

(21) Appl. No.: 11/607,004

(22) Filed: Dec. 1, 2006

(65) Prior Publication Data
US 2007/0146960 A1 Jun. 28, 2007

(30) Foreign Application Priority Data
Dec. 1, 2005 (JP) .............................. 2005-348538

(51) Int. Cl.
*G01N 37/00* (2006.01)
*B05D 1/18* (2006.01)

(52) U.S. Cl. ........................ 73/23.2; 427/443
(58) Field of Classification Search ................. 73/23.2, 73/31.05, 23.31; 427/443
See application file for complete search history.

(56) References Cited

U.S. PATENT DOCUMENTS
2006/0233962 A1 10/2006 Suganuma et al.

FOREIGN PATENT DOCUMENTS
| JP | 09-170089 A | * | 6/1997 |
| JP | 2000-265281 A | * | 9/2000 |
| JP | 2002-12982 A | * | 1/2002 |
| WO | WO 2005/065846 A1 | | 7/2005 |

* cited by examiner

*Primary Examiner*—Michael Cygan
(74) *Attorney, Agent, or Firm*—Sughrue Mion, PLLC (57) ABSTRACT

A gas sensor and method of producing the same, the gas sensor including a sensor element extending along a longitudinal axis of the gas sensor; a metal shell surrounding the sensor element; and a protector fixed on a front portion of the metal shell and covering a front portion of the sensor element which projects from the front end of the metal shell, wherein an oil agent is present on one or both of an inner gas-receiving surface of the metal shell and an inner peripheral surface of the protector in a total amount of less than 0.7 mg.

13 Claims, 3 Drawing Sheets

GAS SENSOR AND METHOD FOR MANUFACTURING THE SAME

BACKGROUND OF THE INVENTION

1. Field of the Invention

This invention relates to a gas sensor adapted for detecting the concentration of a particular gas component in a gas to be measured such as an exhaust gas.

2. Description of the Related Art

A gas sensor installed in an exhaust system of an internal combustion engine has been known, which is used to detect oxygen concentration in exhaust gas for controlling combustion of the internal combustion engine. The oxygen sensor includes a sensor element that extends in an axial direction and is exposed to a gas to be measured at its front end; a tubular metal shell surrounding the sensor element; and a tubular protector that is fitted to the front end of the metal shell and which covers a front end portion of the sensor element protruding from the front end of the metal shell.

Metal parts that constitute the metal shell and the protector of the gas sensor are prepared from a metal material through a plurality of machining processes. During the plurality of machining processes, for instance, a plasticizing process, a cutting process and a grinding process, oil agents such as lubricants, cutting oils and grinding oils are used for lubrication and cooling.

The oil agent adhering to the metal is allowed to remain as is. This is because similar lubrication and cooling is desired in subsequent assembly processes (for instance, crimping of the metal shell and attachment of the protector and the metal shell) of the gas sensor. However, it is well known that when the residual oil agent is present in too much or too little an amount for a subsequent process, the residual oil agent should be partially washed away or more of the same oil agent should be applied so that the amount of adhering oil agent is suitable for the subsequent process. Furthermore, it is known that when the kind of residual oil agent of a processed article is not suitable for the subsequent process and another kind of oil agent is needed, all of the residual oil agent is washed away from the processed article, and an appropriate amount of a different oil agent is applied (JP-A-2005-193183, WO 2005/065846 A1).

If a gas sensor is assembled with the protector and metal shell on which an oil agent remains and then used in an exhaust pipe, the oil agent remaining on the inner peripheral surface of the protector and the inner peripheral surface of the metal shell is gasified. The resultant gas mingles with a gas to be measured to deteriorate the gas detection accuracy. To avoid this problem, JP-A-2005-193183 proposes a gas sensor, in which a metal shell and a protector are heated to gasify the oil agent adhering to the inner peripheral surface of the metal shell and the inner peripheral surface of the protector before the gas sensor is used so that the oil agent is removed in advance. However, in recent years, as emission regulations have become more rigorous, there is a need for higher gas detection accuracy. It is difficult to obtain a gas sensor that can sufficiently meet this need only by heating the gas sensor in advance. In particular, in recent gas sensors, the protector is being increasingly miniaturized. Even when a slight amount of oil agent remains on the inner peripheral surface of the metal shell and the inner peripheral surface of the protector, the gas sensor cannot provide the requisite high accuracy of gas detection due to the gasified oil agent.

The invention has been made to overcome the above-noted problems of the prior art, and an object thereof is to provide a gas sensor that can prevent deterioration of gas detection accuracy due to oil agent adhering to the inner peripheral surface of the protector and the inner peripheral surface of the metal shell.

SUMMARY OF THE INVENTION

The above-described object of the invention has been achieved by providing a gas sensor, comprising: a sensor element extending along a longitudinal axis of the gas sensor; a metal shell surrounding the sensor element; and a protector fixed on a front portion of the metal shell and covering a front portion of the sensor element which projects from a front end of the metal shell, wherein an oil agent is present on one or both of a inner gas-receiving surface of the metal shell and an inner peripheral surface of the protector in a total amount of less than 0.7 mg.

Thus, when the total amount of oil agent present on both the inner gas-receiving surface of the metal shell and the inner peripheral surface of the protector is limited to less than 0.7 mg, an amount of gas resulting from the oil agent, which is gasified during operation of the gas sensor, is sufficiently low so as to prevent the gas detection accuracy from deteriorating. As used herein, the term "oil agent" includes cutting, grinding, lubricating and cooling oils generally employed in metal working operations.

In the invention, an oil agent is applied to at least one of the inner gas-receiving surface of the metal shell and the inner peripheral surface of the protector which are exposed to the gas to be measured. The oil agent is gasified at the operating temperature of the sensor, and the gasified oil agent bleeding into the protector mingles with the gas to be measured inside the protector. However, when the total amount of oil agent is limited to less than 0.7 mg, the gas detection accuracy can effectively be maintained. The effect of the invention is most prominent as to gas sensors which are placed in operation for the first time, for example, when a newly manufactured gas sensor is initially mounted in an exhaust pipe.

In the gas sensor of the invention, preferably, the amount of the oil agent present on the inner peripheral surface of the protector is smaller than the amount present on the inner gas-receiving surface of the metal shell. In assembling the metal shell and the protector, an oil agent is preferably applied to at least one of the metal shell and the protector, for proper setting therebetween. Since an area of the inner peripheral surface of the protector is larger than an area of the inner gas-receiving surface of the metal shell, the oil agent provided on the inner peripheral surface of the protector is likely to have a larger adverse effect on gas detection. Therefore, for reducing the adverse effect on gas detection, the amount of oil agent present on the inner peripheral surface is preferably smaller than on the inner gas-receiving surface of the metal shell. This is done, for example, by washing the protector. The total amount of oil agent present on the inner gas-receiving surface of the metal shell and the inner peripheral surface of the protector can thereby be efficiently reduced.

This invention is especially effective in a sensor where the protector is fixed to a front portion of the metal shell by spot welding or by laser welding. This is because in such a sensor, an oil agent tends to be applied to the metal shell and the protector before welding for the purpose of lubrication or cooling.

Furthermore, this invention provides a gas sensor, which further comprises a sealing member arranged between the inner peripheral surface of the metal shell and the outer surface of the detecting element such that air can pass through the sealing member from the front side to the rear side thereof in an amount of 10 cc/min or less under a condition where the metal shell is heated to 550° C. and air is applied to the front side of the sealing layer at a pressure of 0.4 MPa.

In such a highly airtight gas sensor, a gasified oil agent is unlikely to be discharged through the sealing layer. As the result, the gasified oil agent mixes with the gas to be measured to thereby deteriorate gas detection accuracy. Therefore, in such a highly airtight gas sensor, it is more effective to limit the amount of the inner coating oil agent.

The invention also provides a gas sensor, wherein the metal shell further comprises a crimping portion at a rear end thereof, and the amount of the oil agent present on the inner gas-receiving surface of the metal shell is smaller than the amount of the oil agent present on the outer surface of the crimping portion. In this configuration, an oil agent is appropriately provided on the outer surface of the crimping portion, while the amount of the oil agent can be limited on the inner gas-receiving surface where adhering oil agent may deteriorate gas detection accuracy. Thus, both enhanced accuracy in crimping and enhanced gas detection accuracy can be obtained at the same time.

Furthermore, according to another aspect, the invention provides a gas sensor comprising: a sensor element extending along a longitudinal axis of the gas sensor; a metal shell surrounding the sensor element; and a protector fixed on a front portion of the metal shell and covering a front portion of the sensor element which projects from a front end of the metal shell, wherein an oil agent is present on at least one of an inner gas-receiving surface of the metal shell and an inner peripheral surface of the protector; and wherein an infrared absorbance spectrum obtained by subjecting one or both of the inner gas-receiving surface of the metal shell and the inner peripheral surface of the protector to microscopic infrared spectrometry does not include a peak associated with a bending vibration of CH (hydrocarbon).

Thus, although the infrared absorbance spectrum of the inner gas-receiving surface of the metal shell or the inner peripheral surface of the protector shows some peaks, it does not include a peak associated with a bending vibration of CH, which peak, if present, would indicate a large amount of an oil agent. Using this measurement, the amount of oil agent remaining on the inner peripheral surface of the protector and the inner gas-receiving surface of the metal shell can be limited such that the amount of ensuing gasified oil agent does not adversely affect gas detection accuracy.

The phrase, "the infrared absorbance spectrum obtained by subjecting one or both of the inner gas-receiving surface of the metal shell and the inner peripheral surface of the protector to microscopic infrared spectroscopy does not include a peak associated with a bending vibration of CH (hydrocarbon)" means that when peaks appearing in the infrared absorbance spectrum are identified by their functional group, no peak associated with a bending vibration of CH is present.

According to yet another aspect, the invention provides a method of producing a gas sensor, the gas sensor including: a sensor element extending along a longitudinal axis of the gas sensor; a metal shell surrounding the sensor element; and a protector fixed on a front portion of the metal shell and covering a front portion of the sensor element which projects from a front end of the metal shell;

the method comprising: preparing the metal shell and the protector each having an oil agent provided thereon;

fixing the protector to the metal shell;

assembling the sensor element in the metal shell having the protector fixed thereto; and removing oil agent from at least one of the metal shell and the protector so as to reduce the amount of oil agent present on both the metal shell and the protector to less than 0.7 mg.

Thus, the method of producing a gas sensor includes a step for removing oil agent from the metal shell and/or protector so that the total amount of oil agent present on both the inner gas-receiving surface of the metal shell, which is located forward of a sealing member, and the inner peripheral surface of the protector, is less than 0.7 mg. Accordingly, during operation of the gas sensor, gasified oil agent bleeding toward the inside of the protector can be suppressed to an amount that does not adversely affect gas detection accuracy.

Furthermore, in the invention, the removing step preferably includes a heat treatment process which comprises heating the metal shell and/or the protector. When such a heat treatment process is applied, the oil agent can be efficiently removed from the metal shell and/or the protector even after the metal shell and the protector are assembled.

Furthermore, in order to secure high accuracy of gas detection, the gas sensor further preferably comprises a powdered sealing member arranged between the inner peripheral surface of the metal shell and the outer surface of the detecting element, and the assembling step includes: filling the powder sealing member between the inner peripheral surface of the metal shell and the outer surface of the detecting element, and crimping the rear end portion of the metal shell.

Since there is a step of crimping the rear end portion of the metal shell, an oil agent is preferably applied on the metal shell in advance. However, such an oil agent would likely deteriorate gas detection.

Additionally, by filling the powder sealing member between the inner peripheral surface of the metal shell and the outer surface of the detecting element, and crimping the rear end portion, the airtightness of the gas sensor can be enhanced so that the gas to be measured at the front side of the sealing member does not mix with ambient air at the rear side of the gas sealing member. On the other hand, the gasified oil agent cannot easily be discharged through the sealing layer.

However, in this invention, the amount of the oil agent is reduced to the extent that the gasified oil agent does not deteriorate the accuracy of gas detection even in such a highly airtight gas sensor.

Still further, the invention provides a method of producing a gas sensor further comprising the step of: after the preparing step, washing the protector and the metal shell to remove oil agent, and applying an oil agent on the metal shell so that the amount of oil agent present on the inner gas-receiving surface of the metal shell is in the range of 0.7 to 2 mg. Thus, in the assembling step, although the oil agent is necessarily applied to at least one of the engagement portions of the metal shell and the protector, the oil agent is preferably applied on the metal shell rather than on the protector. This is because an area of the inner peripheral surface of the protector is larger than that of the inner gas-receiving surface of the metal shell and therefore has a larger influence on gas detection. Thus, in this invention, the protector is washed so as to remove the oil agent, while an oil agent is further applied to the metal shell after the metal shell is washed to remove the oil agent. By this method, both enhanced fitting of the protector to the metal shell during the assembling process and enhanced gas detection accuracy are obtained at the same time. However, when less than 0.7 mg of the oil agent is coated, the advantage of the oil agent is not obtained during the machining processes. On the other hand, when the coated amount exceeds 15 mg, the cost increases without further advantage, and it becomes more difficult to remove the oil agent during the following removing step, e.g., during the heat treatment process. Since the oil agent coated in an amount within the above range is removed in the removing step, the gas sensors thus produced can exhibit sufficient gas detection accuracy.

In order to enhance the fixing strength of the protector, the fixing step preferably includes welding the protector to the metal shell.

Furthermore, in yet another aspect, the invention provides a method of producing a gas sensor, the gas sensor including: a sensor element extending along a longitudinal axis of the gas sensor; a metal shell surrounding the sensor element and having a crimping portion at a rear end thereof; and a protector fixed on a front portion of the metal shell and covering a front portion of the sensor element which projects from a front end of the metal shell, the method comprising: preparing the metal shell and the protector each having an oil agent provided thereon; washing the metal shell and the protector so as to remove oil agent; and applying an oil agent on an outer surface of the crimping portion of the washed metal shell.

According to the above method, the inner gas-receiving surface of the metal shell and the inner surface of the protector are washed to remove oil agent in the washing step. Since the amount of oil agent remaining after the washing step is smaller than the amount of oil agent remaining after a heating treatment, the washing step is more efficient and effective than heat treatment. On the other hand, in the crimping process, an oil agent is required for proper crimping. Therefore, by applying an oil agent on the outer surface of the crimping portion of the metal shell which was washed in the washing process, the crimping accuracy can be secured without deteriorating gas detection accuracy.

Additionally, in yet another aspect, the invention provides a gas sensor comprising: a sensor element extending along a longitudinal axis of the gas sensor; a metal shell surrounding the sensor element; a protector fixed on a front portion of the metal shell and covering a front portion of the sensor element which projects from a front end of the metal shell; and a sealing member provided between an inner peripheral surface of the metal shell and an outer surface of the detecting element, wherein an oil agent is present on one or both of an inner gas-receiving surface of the metal shell and an inner peripheral surface of the protector in a total amount of 0.7 mg to 2 mg, and wherein air can pass through the sealing member from the front side to the rear side thereof in an amount of from more than 10 cc/min to 50 cc/min under a condition where the metal shell is heated to 550° C. and air is applied to the front side of the sealing layer at a pressure of 0.4 MPa.

In such a relatively low airtight gas sensor, the amount of the remaining oil agent can be increased to 0.7 mg to 2 mg. This is because a gasified oil agent can be discharged through the sealing layer so that the adverse effect of the gasified oil agent can be reduced. However, since the discharge amount of a gasified oil agent through the sealing layer is limited, the gasified oil agent is likely to deteriorate the gas detection accuracy when the amount of the oil agent is more than 2 mg, even in such a relatively low airtight gas sensor. If the air flow exceeds 50 cc/min, the gas detection accuracy could be deteriorated by ambient air passing through the sealing layer to mingle with the gas to be measured at the front side of the sealing layer.

DESCRIPTION OF THE PREFERRED EMBODIMENTS

A mode for carrying out a first embodiment of a gas sensor according to the invention will now be described with reference to the drawings. However, the present invention should not be construed as being limited thereto.

Figure 1:
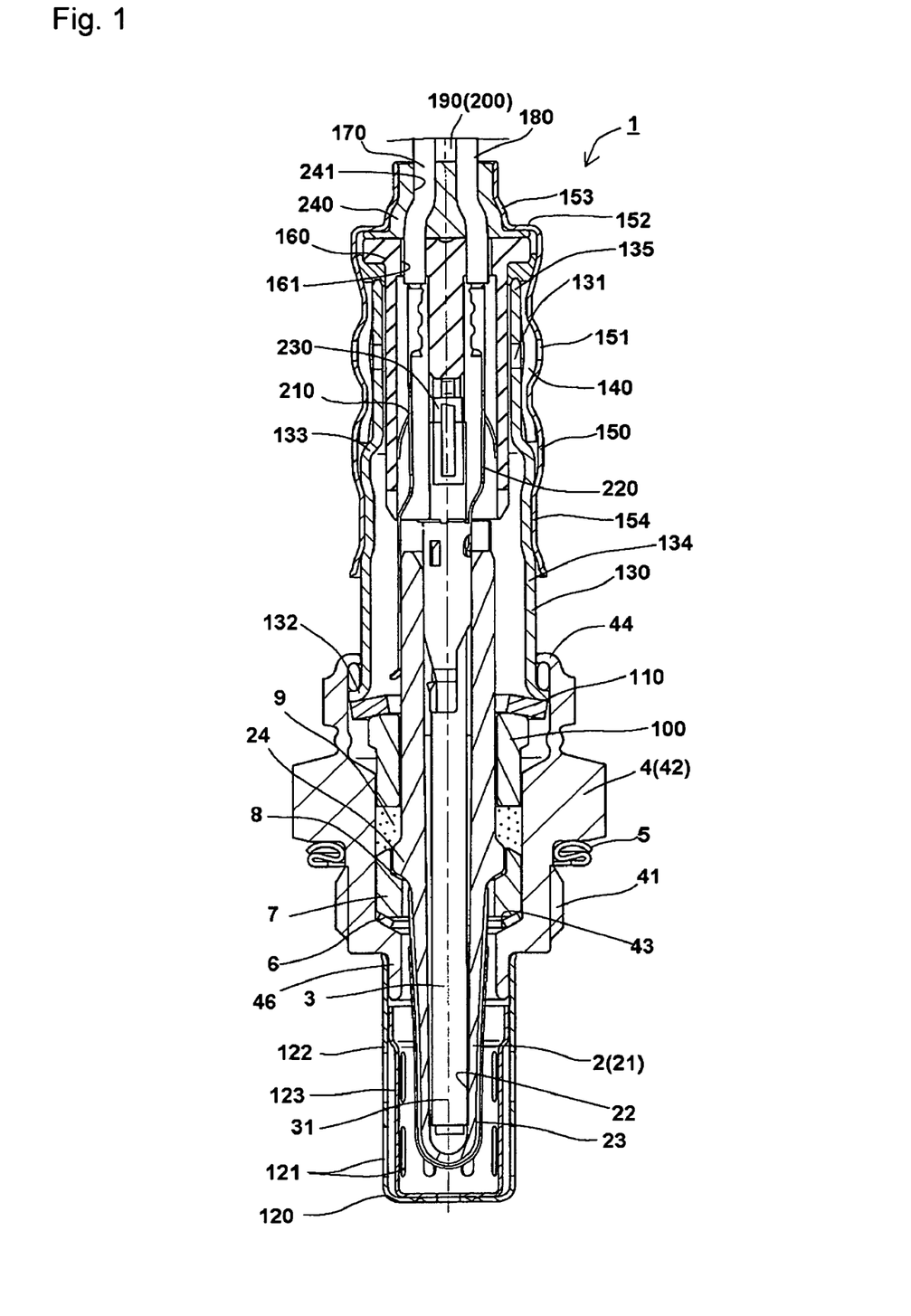
FIG. 1 is a sectional view showing a gas sensor according to first and second embodiments of the invention.
Figure 2:
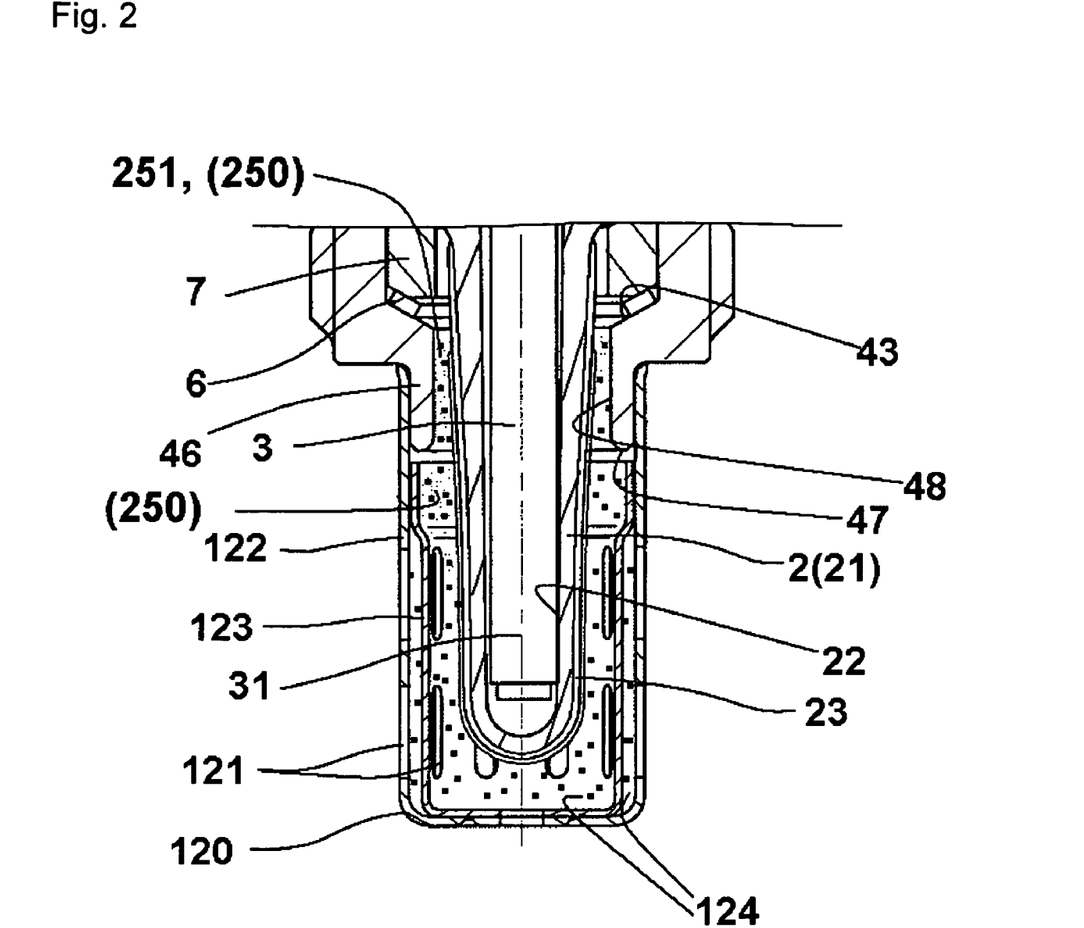
FIG. 2 is an enlarged sectional view of an essential portion of the gas sensor of the first embodiment.

First, a structure of a gas sensor 1 will be described by way of example with reference to FIGS. 1 and 2. FIG. 1 is a sectional view showing the entire configuration of a gas sensor 1 of the embodiment.

As shown in FIG. 1, a gas sensor 1 includes a bottomed cylindrical sensor element 2 closed at its front end, a ceramic heater 3 inserted into the sensor element 2 and a metal shell 4 that supports the sensor element 2 arranged inside thereof. In the description, along the longitudinal axis of the sensor element 2 shown in FIG. 1, the portion toward the front end (a closed side, the lower side in the drawing) exposed to a gas to be measured (exhaust gas) is taken as "the front portion" and the portion opposite thereto (the upper side in the drawing) is taken as "the rear portion".

The sensor element 2 includes a solid electrolyte body 21 made of partially stabilized zirconia as its main component, in which yttria is dissolved as a stabilizer and which has oxygen ion conductivity, an internal electrode 22 made of Pt or a Pt alloy provided on the inner surface of the solid electrolyte body 21, and an external electrode 23 formed on the outer surface of the solid electrolyte body 21. A flange portion 24 projecting toward an outer side in a radial direction is provided at roughly the midpoint in the axis of the sensor element 2. Furthermore, the ceramic heater 3 has a pole shape and a heat-generating portion 31 comprising a heat-generating resistor inside. The ceramic heater 3 is energized through heater lead wires 190 and 200 described below to heat and thus activate the sensor element 2.

Next, a metal shell 4 and a protector 120 will be described in detail.

The metal shell 4 is made of SUS430 and includes a threaded portion 41 for fixing the gas sensor 1 to an exhaust pipe, and a hexagonal portion 42 to which a fixing tool is applied when the exhaust pipe is fixed. Furthermore, a gasket 5 is disposed to. the front end side of the hexagonal portion 42. Still further, a metal shell step portion 43 is disposed on the inner periphery of the metal shell for receiving a packing 6. An alumina support portion 7 is supported through the packing 6 by the metal shell step portion 43. The flange portion 24 of the sensor element 2 is supported on the support member 7 through packing 8. Furthermore, a powdered seating member 9 is disposed between the inner surface of the portion of the metal shell 4 and the outer surface of the sensor element 2. Still further, to the rear of the powdered sealing member 9, a sleeve 100 and an annular ring 110 are sequentially arranged.

Furthermore, so as to cover a front portion of the sensor element 2, a protector 120 made of SUS310 is disposed and fixed to the front end portion 46 of the metal shell 4 by spot welding. The protector 120 is formed to have a dual structure comprising an outer protector 122 and an inner protector 123 that have a plurality of gas inlets 121 in their respective circumferences.

The metal shell and the protector are, as will be described below, prepared through a plurality of processes from metal material. Also, a first oil agent 250 for lubrication and cooling during the mechanical processes and a second oil agent 251 used thereafter in the crimping of the metal shell 4 are coated. For this, as shown in FIG. 2, on at least part of the inner gas-receiving surface 48 from packing 6 to the front end 47 of the metal shell 4, which is exposed to the gas to be measured, and the inner peripheral surface 124 of the protector 120 (the inner peripheral surface of the outer protector 122 and the inner peripheral surface of the inner protector 123), the first and second oil agents 250, 251 are applied, the total amount being limited to less than 0.7 mg.

Thus, when the total amount of the first and second oil agents 250, 251 applied to the inner gas-receiving surface 48 of the metal shell 4 and of the inner peripheral surface 124 of the protector 120 is limited to less than 0.7 mg, an amount of gasified oil agent that bleeds inside the protector 120 during the use of the gas sensor 1 can be suppressed so as not to adversely affect gas detection accuracy.

The first oil agent 250 can be used for lubrication and cooling in a plurality of machining processes when the metal shell 4 and the protector 120 are prepared. The first oil agent 250 specifically comprises mineral oil. On the other hand, the second oil agent 251 is used when the metal shell 4 is crimped and is likely to adversely affect gas detection accuracy as well as the first oil agent 250. However, the oil agent 250 provided on the inner gas-receiving surface 48 of the metal shell 4 and the inner peripheral surface 124 of the protector 120 is removed in a washing process, and the oil agent 251 coated on the inner gas-receiving surface 48 of the metal shell 4 is removed in a heat treatment process so that the total amount of the first and second oil agents 250, 251 present on the inner gas-receiving surface 48 of the metal shell 4 and the inner peripheral surface 124 of the protector 120 is less than 0.7 mg (upon completion of the gas sensor).

In this embodiment, since the first oil agent 250 is removed from the protector 120 by washing and the second oil agent 251 is not applied to the protector 120, the amount of oil agent which should be removed in the following heat treatment can be reduced in advance. The amount of the first oil agent remaining after washing is 0.2 mg or less. Since the surface area of the inner peripheral surface 124 of the protector 120 is relatively large, the effect of washing the protector 120 in advance is relatively large. On the other hand, the second oil agent 251 on the metal shell 4 works when the protector 120 is fixed to the metal shell 4 and when the rear end portion 44 of the metal shell 4 is crimped.

Figure 3:
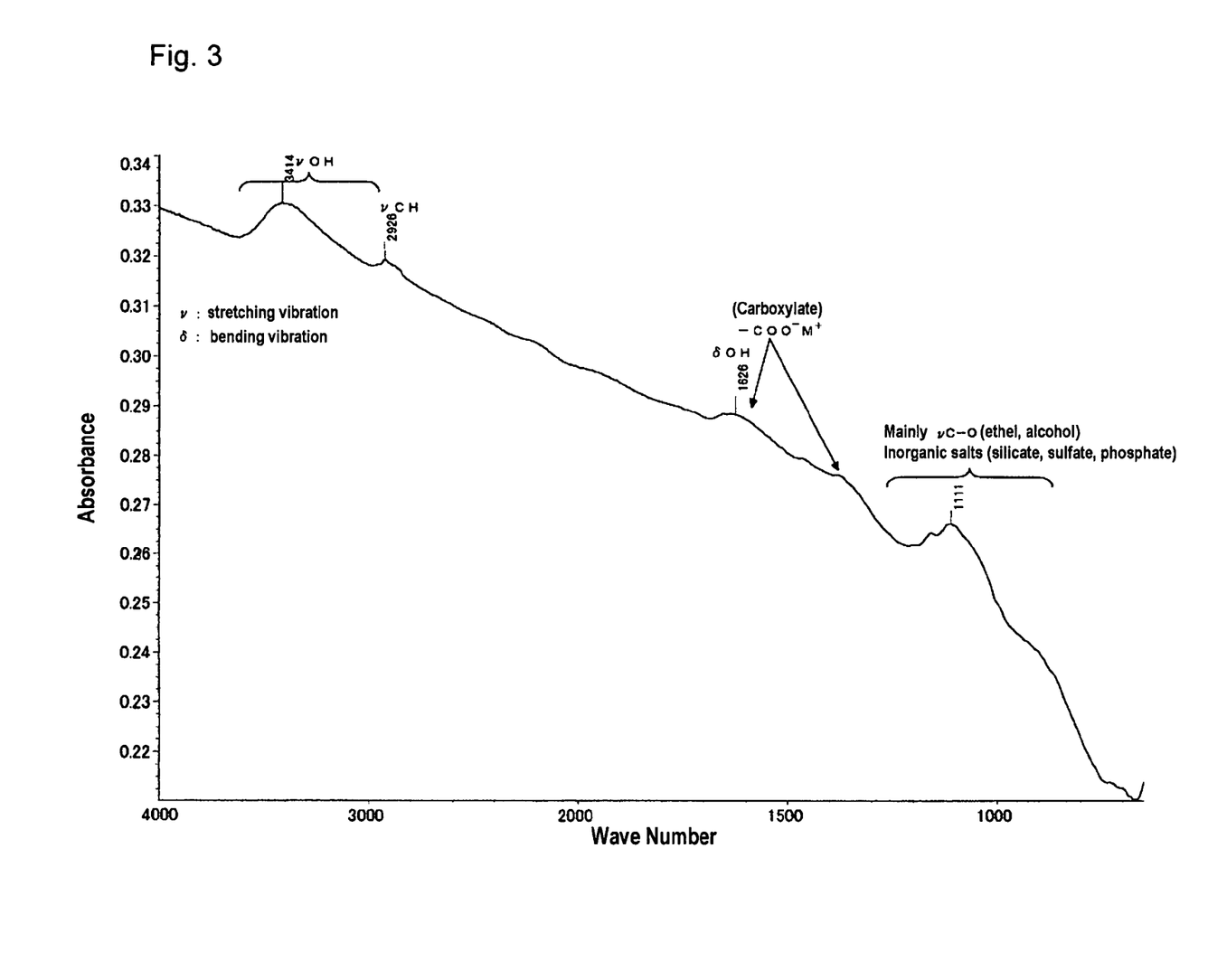
FIG. 3 is an infrared absorption spectrum obtained by microscopic infrared spectrometry of a metal shell of the gas sensor of the first embodiment.

Furthermore, when the inner peripheral surface 124 of the protector 120 and the inner peripheral surface 48 of the front portion of the metal shell 4 are analyzed by microscopic infrared spectroscopy, an infrared absorption spectrum such as shown in FIG. 3 can be obtained. In the microscopic infrared spectroscopy with a microscopic infrared spectrometer (trade name: IRµs, produced by Spectra-Tech Corp.), an analysis was carried out based on the measurement conditions given below.

Light source: glow bar, detector: Narrow•MCT (HgCdTe), purge: nitrogen gas, resolving power: 8 cm$^{-1}$, cumulative number: 2048 times or less, measurement mode: transmission mode, measurement range of wave number: 4000 to 650 cm$^{-1}$ According to FIG. 3, the infrared absorbance spectrum shows some peaks generated correspond to stretching vibration of OH, stretching vibration of CH, and carboxylate, respectively. However, no peaks associated with bending vibration of CH are observed, which peaks would indicate the presence of a large amount of oil agent. The fact that bending vibration of CH is not among any of the peaks appearing in the infrared absorbance spectrum means that the amount of the remaining oil agent is small enough to secure good gas detection accuracy.

Returning to FIG. 1, a front portion of inner cylinder member 130 is arranged inside the rear portion of the metal shell 4. The inner cylinder member 130, with an open end (at its front edge 132) expanded in diameter and abutting an annular ring 110, is fixed to the metal shell 4 by crimping the rear end 44 of the metal shell 4 so that its end surface faces the front portion of the inner cylinder member 130. When the rear end 44 of the metal shell 4 is crimped, a powdered sealing member 9 is filled and compressed between the sleeve 100 and the support member 7, to thereby airtightly hold the sensor element 2 inside the tubular metal shell 4.

Since the gas sensor 1 has a highly airtight structure where the support member 7, the powdered sealing member 9, and the sleeve 100 are crimped between the step portion 43 and the rear portion of the metal shell 4, the gasified first and second oil agents 250, 251 cannot be discharged through the air tight structure between the sensor element 2 and the metal shell 4. Therefore, the gasified oil agents are likely to flow toward the front side and to mingle with the gas to be measured. However, in this embodiment, the amount of oil agents formed on the inner surface is so small as not to adversely affect gas detection.

The inner cylinder member 130 has a shoulder portion 133 roughly in the axial middle and thus located between a front end portion 134 and a rear portion 135. The rear portion 135 is formed smaller in both its inner diameter and outer diameter than the front portion 134, and the inner diameter of the rear portion is formed slightly larger than the outer diameter of a separator 160. Furthermore, the rear portion 135 has a plurality of air inlet holes 131 disposed at a predetermined interval along the circumference.

An outer cylinder member 150 is formed into a tube and has a front end portion 154 fixed to the front portion 134 of the inner cylinder member 130 and a rear portion 153 that airtightly fastens a seal member 240. Furthermore, a plurality of air inlet holes 151 is formed at a predetermined interval along the circumference.

A water-repellent filter 140 is disposed between the air inlet holes 131 of the inner cylinder member 130 and the air inlet holes 151 of the outer cylinder member 150. The filter 140 is made of, for instance, porous fibrous structure polytetrafluoroethylene (trade name: GORETEX, produced by Japan GORETEX Corp.).

The filter 140 is fastened by crimping the outer cylinder member 150 at the front and the rear side of the air inlet holes 151. Furthermore, further to the front than the filter 140, the outer cylinder member 150 and the inner cylinder member 130 are directly crimped and thereby the outer cylinder member 150 and the inner cylinder member 130 are fastened.

Thereby, air used as a reference gas is introduced through the air inlet holes 151, the filter 140 and the air inlet holes 131 to the inside of the inner cylinder member 130, and then is introduced inside the sensor element 2.

Furthermore, a separator 160 is disposed inside the inner cylinder member 130. The separator 160 has holes 161 in which element lead wires 170 and 180 and heater lead wires 190 and 200 are inserted and connected with terminal fittings 210 and 220, and a pair of heater terminal fittings 230, 230 respectively. Thus, the lead wires 170 and 180 are connected with the external electrode 23 and the internal electrode 22 of the sensor element 2. On the other hand, the heater lead wires 190 and 200 are connected to the heat-generating resistor of the ceramic heater 3.

A seal material 240 made of a fluororubber, having excellent heat resistance, is fixedly arranged in the rear portion 153 of the outer cylinder member 150. The seal member 240 has four lead wire insertion holes 241 in which the element lead wires 170 and 180 and heater lead wires 190 and 200 are inserted.

Next, a production method of the gas sensor 1 of the embodiment will be described in detail.

First, applying a first oil agent 250 for lubrication and cooling, a plurality of machining processes (plastic process and grinding process) is applied to steel SUS430 to prepare a tubular metal shell 4 having a hexagonal portion 42, a screw portion 41, a step portion 43 and a front end portion 46 (preparing step). Since the first oil agent 250 remains on the surface of the processed metal shell 4, the metal shell 4 is dipped in a degreasing solution to remove the first oil agent 250 on the metal shell 4 to the extent possible (washing step).

Second, the washed metal shell 4 is dipped in an oil agent solution to obtain a metal shell 4 coated with a second oil agent 251. The second oil agent 251 includes an aqueous oil agent and an active agent, which are blended and dissolved in warm water. The aqueous oil agent is an aqueous solution of about 30 wt % oil components with alkylamine oxide as an additive, the blending ratio being 50 to 60 ml/l. Furthermore, the active agent is a nonionic surfactant and a blending ratio thereof is 13 to 20 ml/l. The temperature range of the warm water is 50 to 60° C.

On the other hand, the protector 120 can be obtained in the following process. Like the metal shell 4, to steel SUS310, a plurality of machining processes (plastic process and punching process) is applied to prepare an internal protector 123 and an external protector 122, each of which is provided with a plurality of gas inlet holes 121. Since, during the plurality of these machining processes (plastic processing, grinding) as well, the first oil agent 250 is used for lubrication and cooling, on surfaces of the processed outer protector 122 and inner protector 123 as well, the first oil agent 250 remains (preparing step). Therefore, the outer protector 122 and the inner protector 123 are dipped in a degreasing solution and then rinsed to remove the first oil agent 250 on the metal shell 4 to the extent possible, e.g. to 0.2 mg or less (washing step). Then, the inner protector 123 is inserted inside the outer protector 122, followed by spot welding to fasten each other to obtain the protector 120. A process for obtaining the metal shell 4 and protector 120 corresponds to the preparing step.

At that time, on the inner peripheral surface 48 of the front portion of the metal shell 4, which will be the inner gas receiving surface, and the inner peripheral surface 124 of the protector 120, 0.7 mg to 2 mg of the oil agent is coated in total. Thus, since the first oil agent 250 is coated in the range of 0.7 mg to 2 mg in the oil agent applying step, the protector 120 and the metal shell 4 can be efficiently prepared through a plurality of machining processes from metal.

Third, the rear portion of the protector 120 is fitted around the outer periphery of the front portion 46 of the metal shell 4 to overlap respective portions, and the overlapping portions are spot welded to fasten the protector 120 and the metal shell 4 (fixing step).

On the other hand, 5% by mol of yttria is added to zirconia, granulated, formed into a bottomed cylinder closed at its front end as shown in FIG. 1, and sintered in an electric furnace at a temperature in the range of 1400 to 1600° C., to thereby obtain a solid electrolyte 21. Then, on an outer peripheral surface of the solid electrolyte 21, a platinum external electrode 23 is formed by vapor deposition or chemical plating, while on an inside surface of the solid electrolyte 21 as well, similarly, by vapor deposition or chemical plating, an internal electrode 22 is formed, to thus obtain a sensor element 2.

Fourth, inside the metal shell 4 to which the protector 120 is welded, a packing 6, a support member 7, a packing 8, a sensor element 2, a powdered sealing member 9, a sleeve 100 and an annular ring 110 are arranged in this order (assembling step). The packing 6 is supported by the step portion 43 of the metal shell 4. Then, with the open front end 132 of an inner cylinder member 130 abutting an annular ring 110, the rear portion 44 of the metal shell 4 is crimped forwardly and inwardly, to prepare a lower assembly.

Fifth, the lower assembly is heat treated to remove the second oil agent 251 from the metal shell 4 (removing step). Specifically, the temperature of the heat treatment is increased to 430° C., maintained for 60 minutes at 430° C., and the assembly is left to cool. With this heat treatment process, the amount of remaining oil agent 251 can be reduced to less than 0.7 mg. During this heat treatment, the first oil agent 250 which may still remain after the washing process can also be removed.

Since the total amount of the first and second oil agents 250, 251 remaining on the inner gas receiving surface 48 of the metal shell 4 and inner peripheral surface 124 of the protector 120 is less than 0.7 mg, the gas detection is not influenced by the first and second oil agents 250, 251.

Sixth, the element lead wires 170 and 180, respectively, are connected to the terminal fittings 210 and 220 and the heater lead wires 190 and 200 are connected to the heater terminal tag 230 of the ceramic heater 3. Then, with the ceramic heater 3 arranged inside the terminal fitting 220, the lead wires 170, 180, 190 and 200, respectively, are inserted in the separator lead wire insertion holes 161 of the separator 160. Then, with the lead wires 170, 180, 190 and 200, respectively, inserted in the lead wire insertion holes 241 of the seal member 240, the front end surface of the seal member 240 is moved until the front end surface abuts the rear end surface of the separator 160. Thus, an upper assembly is prepared.

Seventh, the separator 160 of the upper assembly is located inside the rear portion 135 of the inner cylinder member 130, in the lower assembly. Thereby, the terminal fitting 220 as well as the ceramic heater 3 is inserted into the cup-shaped sensor element 2 for electrical connection to the internal electrode 22. Furthermore, the terminal fitting 210 engages the outer surface of the sensor element 2 so as to be electrically connected to the external electrode 23.

Eighth, the filter 140 is disposed to surround the air inlet holes 131 of the inner cylinder member 130. Then, the outer cylinder member 150 is moved, with the respective lead wires 170, 180, 190 and 200 inserted inside the outer cylinder member itself, from the rear of the seal member 240, until the outer cylinder member 150 overlaps with the outside of the front end portion 134 of the inner cylinder member 130. Then, the outer cylinder member 150 and a grommet 240 are crimped respectively to complete a gas sensor 1.

An embodiment of the invention has been described above. However, the invention is not limited thereto, and can be variously modified so long as the objects of the invention can be achieved.

For example, as a modified embodiment of the invention, the amount of oil agent remaining on the protector and the inner gas-receiving surface of the metal shell can be relatively high, i.e., from 0.7 mg to 2.0 mg, while the airtightness of a sealing portion provided between the sensor element and the metal shell is made relatively low.

A mode for carrying out the invention of a second embodiment of a gas sensor according to the invention will now be described with reference to FIG. 1.

In the second embodiment, like the first embodiment, the metal shell 4 and the protector 120 on which the first oil agent 250 is provided are dipped in a degreasing solution and then rinsed so as to remove the first oil agent 250 until the total remaining amount of the first oil agent 250 is 0.2 mg or less (preparing step, washing step).

Unlike the first embodiment where the protector 120 is fixed to the metal shell 4 after the second oil agent 251 is applied to the metal shell 4, the protector is fixed to the metal shell 4 without applying the second oil agent 251 on the protector 251 in the second embodiment. The front end portion of the metal shell 4 is inserted into the opening of the protector 120, and the overlapping portion is fixed by spot welding (assembling process).

Next, a second oil agent 251 is applied only on the outer surface of the rear end portion (crimping portion) 44 of the metal shell 4 (a second oil agent applying step) in order to crimp the rear end portion 44 of the metal shell 4 in the following crimping process.

Then, a packing 6, a support member 7, a packing 8, a sensor element 2, a powder sealing member 9, a sleeve 100 and a annular ring 120 are inserted into the assembly of the protector 110 and the metal shell 4. The step portion 43 supports the packing 6. With the open front end 132 of an inner cylinder member 130 abutting an annular ring 110, the rear end portion 44 of the metal shell is crimped forwardly and inwardly, to prepare a lower assembly.

In this embodiment, since no oil agent is applied on either of the inner gas-receiving surface 48 of the metal shell 4 and the inner peripheral surface 124 of the protector 120 after the first oil agent 250 is removed therefrom, the gas detection accuracy of the sensor is not deteriorated by an oil agent.

Furthermore, when the second oil agent 251 is applied only on the outer surface of the rear end portion 44 of the metal shell 4, the second oil agent 251 need not be removed in a heating treatment. However, this does not exclude the use of a heat treatment. For example, if the amount of the first oil agent 250 which still remains after the washing process is not negligible, a heating process can be applied to the remaining oil agent to further reduce the remaining amount. Such a heating process after washing can be simplified because most of the oil agent has already been removed in the former washing process.

Furthermore, in the above embodiments, the fitting inner side step portion 43 of the metal shell 4 supports the sensor element 2 through the packing 6, support member 7 and packing 8. However, the invention is not limited thereto, and the sensor element 2 may be directly supported by the step portion 43 of the metal shell 4. In this case, the site where the sensor element 2 abuts the step portion 43 becomes the support portion 45.

Furthermore, in the above embodiments, the protector 120 has a dual structure made of an outer protector 122 and an inner protector 123. However, the invention is not limited thereto, and a single structure can be used for the protector.

Still further, in the above embodiments, a bottomed tubular sensor element 2 was used. However, the invention is not limited thereto, and a planar sensor element may be used.

Furthermore, in the above embodiments, the first oil agent 250 is coated on both the metal shell 4 and the protector 120. However, the invention is not limited thereto, and the oil agent may be coated on the metal shell 4 only or the protector 120 only.

This application is based on Japanese Patent Application No. JP 2005-348538 filed Dec. 1, 2005, incorporated herein by reference in its entirety.

What is claimed is:

1. A gas sensor, comprising:
a sensor element extending along a longitudinal axis of the gas sensor;
a metal shell surrounding the sensor element; and
a protector fixed on a front portion of the metal shell and covering a front portion of the sensor element which projects from the front end of the metal shell,
wherein an oil agent is present on one or both of an inner gas-receiving surface of the metal shell and an inner peripheral surface of the protector in a total amount of less than 0.7 mg,
wherein the amount of oil agent present on the inner peripheral surface of the protector is smaller than the amount of oil agent present on the inner gas-receiving surface of the metal shell.

2. The gas sensor according to claim 1, wherein the protector is fixed on the front portion by welding.

3. The gas sensor according to claim 1, wherein the gas sensor further comprises a sealing member arranged between the inner peripheral surface of the metal shell and the outer surface of the detecting element such that air can pass through the sealing member from the front side to the rear side thereof in an amount of 10 cc/min or less under a condition where the metal shell is heated to 550° C. and air is applied to the front side of the sealing layer at a pressure of 0.4 MPa.

4. The gas sensor according to claim 1, wherein the metal shell further comprises a crimping portion at a rear end thereof, and the amount of oil agent present on the inner gas-receiving surface of the metal shell is smaller than the amount of oil agent present on the outer surface of the crimping portion.

5. A gas sensor, comprising:
a sensor element extending along a longitudinal axis of the gas sensor;
a metal shell surrounding the sensor element; and
a protector fixed on a front portion of the metal shell and covering a front portion of the sensor element which projects from a front end of the metal shell,
wherein an oil agent is present on one or both of an inner gas-receiving surface of the metal shell and an inner peripheral surface of the protector; and
wherein an infrared absorbance spectrum obtained by subjecting one or both of the inner gas-receiving surface of the metal shell and the inner peripheral surface of the protector to microscopic infrared spectrometry does not include a peak associated with a bending vibration of CH, and
wherein the metal shell further comprises a crimping portion at a rear end thereof, and the amount of oil agent present on the inner gas-receiving surface of the metal shell is smaller than the amount of oil agent present on the outer surface of the crimping portion.

6. A method of producing a gas sensor, the gas sensor including:
a sensor element extending along a longitudinal axis of the gas sensor;
a metal shell surrounding the sensor element; and
a protector fixed on a front portion of the metal shell and covering a front portion of the sensor element which projects from a front end of the metal shell,
the method comprising:
preparing the metal shell and the protector each having an oil agent provided thereon;
fixing the protector to the metal shell;
assembling the sensor element in the metal shell having the protector fixed thereto; and
removing oil agent from at least one of the metal shell and the protector so as to reduce the total amount of oil agent present on both the metal shell and the protector to less than 0.7 mg,
wherein said removing step comprises heating at least one of the metal shell and the protector.

7. The method of producing a gas sensor according to claim 6, wherein the gas sensor further comprises a powdered sealing member arranged between the inner peripheral surface of the metal shell and the outer surface of the sensor element, and said assembling step comprises: filling the powder sealing member between the inner peripheral surface of the metal shell and the outer surface of the detecting element, and crimping the rear end portion of the metal shell.

8. The method of producing a gas sensor according to claim 7, which further comprises:
   after the preparing step, washing the protector and the metal shell to remove oil agent, and
   applying an oil agent on the metal shell so that the amount of oil agent present on the inner gas-receiving surface of the metal shell is in the range of 0.7 to 2 mg.

9. The method of producing a gas sensor according to claim 6, wherein the fixing step comprises welding the protector to the metal shell.

10. A gas sensor, comprising:
    a sensor element extending along a longitudinal axis of the gas sensor;
    a metal shell surrounding the sensor element;
    a protector fixed on a front portion of the metal shell and covering a front portion of the sensor element which projects from a front end of the metal shell; and
    a sealing member arranged between the inner peripheral surface of the metal shell and the outer surface of the detecting element,
    wherein an oil agent is present on one or both of an inner gas-receiving surface of the metal shell and an inner peripheral surface of the protector in a total amount of 0.7 mg to 2 mg, and
    wherein air can pass through the sealing member from the front side to the rear side thereof in an amount of from more than 10 cc/min to 50 c/min under a condition where the metal shell is heated to 550° C. and air is applied to the front side of the sealing layer at a pressure of 0.4 MPa.

11. A gas sensor, comprising:
    a sensor element extending along a longitudinal axis of the gas sensor;
    a metal shell surrounding the sensor element; and
    a protector fixed on a front portion of the metal shell and covering a front portion of the sensor element which projects from the front end of the metal shell,
    wherein an oil agent is present on one or both of an inner gas-receiving surface of the metal shell and an inner peripheral surface of the protector in a total amount of less than 0.7 mg, and
    wherein the gas sensor further comprises a sealing member arranged between the inner peripheral surface of the metal shell and the outer surface of the detecting element such that air can pass through the sealing member from the front side to the rear side thereof in an amount of 10 cc/mm or less under a condition where the metal shell is heated to 550° C. and air is applied to the front side of the sealing layer at a pressure of 0.4 MPa.

12. A gas sensor, comprising:
    a sensor element extending along a longitudinal axis of the gas sensor;
    a metal shell surrounding the sensor element; and
    a protector fixed on a front portion of the metal shell and covering a front portion of the sensor element which projects from the front end of the metal shell, and
    wherein an oil agent is present on one or both of an inner gas-receiving surface of the metal shell and an inner peripheral surface of the protector in a total amount of less than 0.7 mg,
    wherein the metal shell further comprises a crimping portion at a rear end thereof, and the amount of oil agent present on the inner gas-receiving surface of the metal shell is smaller than the amount of oil agent present on the outer surface of the crimping portion.

13. A method of producing a gas sensor, the gas sensor including:
    a sensor element extending along a longitudinal axis of the gas sensor;
    a metal shell surrounding the sensor element; and
    a protector fixed on a front portion of the metal shell and covering a front portion of the sensor element which projects from a front end of the metal shell,
    the method comprising:
    preparing the metal shell and the protector each having an oil agent provided thereon;
    fixing the protector to the metal shell;
    assembling the sensor element in the metal shell having the protector fixed thereto; and
    removing oil agent from at least one of the metal shell and the protector so as to reduce the total amount of oil agent present on both the metal shell and the protector to less than 0.7 mg,
    wherein the gas sensor ftirther comprises a powdered sealing member arranged between the inner peripheral surface of the metal shell and the outer surface of the sensor element, and said assembling step comprises: filling the powder sealing member between the inner peripheral surface of the metal shell and the outer surface of the detecting element, and crimping the rear end portion of the metal shell.

* * * * *